United States Patent [19]

McAndless et al.

[11] Patent Number: 4,869,117

[45] Date of Patent: Sep. 26, 1989

[54] "POLYMER PACKED MINITUBE VAPOR SAMPLING SYSTEM"

[75] Inventors: John M. McAndless; James R. Hancock, both of Medicine Hat; Donald B. Barnett, Saskatoon; Orville J. Olm, Saskatoon; Terry J. A. Locke, Saskatoon; John Maybank, Saskatoon, all of Canada

[73] Assignee: Her Majesty the Queen in Right of Canada as represented by the Minister of National Defence, Canada

[21] Appl. No.: 184,810

[22] Filed: Apr. 22, 1988

[51] Int. Cl.⁴ .............................................. G01N 1/24
[52] U.S. Cl. .................................. 73/864.34; 73/863.21
[58] Field of Search ............. 73/863.1, 863.21, 863.25, 73/863.71, 863.83, 863.84, 864.34, 864.35, 864.91; 55/270

[56] References Cited

U.S. PATENT DOCUMENTS

| | | | |
|---|---|---|---|
| 3,540,261 | 11/1970 | Scoggins | 73/863.31 |
| 3,884,081 | 5/1975 | Griffith | 73/863.31 |
| 3,921,456 | 11/1975 | Newcomb, Jr. et al. | 73/864.34 |
| 4,091,674 | 5/1978 | Amey | 73/864.34 |
| 4,584,887 | 4/1986 | Galen | 73/864.34 |

FOREIGN PATENT DOCUMENTS

0715960 2/1980 U.S.S.R. ........................... 73/864.34

Primary Examiner—Robert R. Raevis
Attorney, Agent, or Firm—Roylance, Abrams, Berdo & Goodman

[57] ABSTRACT

An air sampler includes a magazine having a plurality of sampling tubes, and an inlet and an outlet at a sampling position. A tube advancing mechanism sequentially advances the sampling tubes to and from the sampling position. A tube sealing arrangement is provided at the sampling position. An air pump draws air through the inlet, a sampling tube at the sampling position, and the outlet. A control sequentially operates the magazine, obtaining air samples within the sampling tubes.

11 Claims, 9 Drawing Sheets

"POLYMER PACKED MINITUBE VAPOR SAMPLING SYSTEM"

FIELD OF THE INVENTION

The present invention relates to the trapping and collecting of airborne contaminants for subsequent analysis.

BACKGROUND

The trapping and collection of airborne contaminants in the form of gases, vapours or aerosols is of importance in a number of fields. For example, contaminants may be collected to determine the downwind spread of herbicides or pesticides from a cross-spraying operation, to determine industrial compliance with air quality standards, to monitor workplace air quality or for controlling the use of toxic materials and to monitor and identify toxic substances released during military encounters.

The current techniques for collecting air samples are:

1. By using liquid-filled impingers or bubblers. Air is drawn ("bubbled") through the liquid which partially or completely dissolves the contaminants and thus removes them from the air stream. The solution is subsequently analyzed by injection into, e.g., a gas chromatograph.

2. By using tubes packed with a solid, porous absorbent. The solid material retains contaminants by, for example, physical inclusion in pores or electrostatic attraction at active polar sites on the surface of the solid when air is drawn through the tubes. The solid material is subsequently solvent extracted and the extracts analyzed, or the material is heated to thermally desorb the trapped contaminants into an appropriate apparatus for analysis.

3. By collecting sample volumes of the air in suitable containers such as large bags or gas syringes. The air is withdrawn from the collection container using a small gas tight syringe and injected into an analysis apparatus.

4. By drawing air continuously through analyzers which monitor contaminant concentration in real time or near real time.

All of these techniques suffer from certain disadvantages. For example, bubblers are relatively large and cumbersome devices that are difficult to use in field trials or large scale sampling networks. In addition, only a very small aliquot of the trapping solvent or liquid charge of the bubbler is needed to perform an analysis. This severely restricts the sensitivity of analysis methods based on bubbler sample collection.

While sample tubes packed with a solid adsorbent overcome many disadvantages of the bubbler sampling system, they suffer from other disadvantages. Standard solid sorbent tubes are of a relatively large size, which is dictated by the requirement to either take air samples over long periods of time or to sample relatively high concentrations of contaminants. A large quantity of solid adsorbent is required to prevent exceeding the retention capacity of the adsorbent. Effective thermal desorption of such tubes is difficult to achieve since the sheer bulk of the asorbent material prevents the material from being heated in a uniform fashion. Uneven heating produces non-instantaneous desorption of the sample components and relatively broad chromatographic "peaks". In addition, with current solid adsorbent packed tube technology, the outer surfaces of the sample tubes are usually exposed to the ambient atmosphere. This can create problems with respect to trace analysis as any contaminant retained on the outer surface of the tube from handling or exposure may enter into the analytical process.

A field sampling system based on large volume air collection bags is bulky, labour intensive in preparation and operation and requires manual techniques in transferring air samples from the collection devices to the analytical instrumentation.

Real time monitors are generally single point samplers. While they can be used with a manifold to sample a few points in sequence, for a large field trial or ambient air quality study, many such devices would be required to simultaneously sample the air at many different locations. The cost of this would be prohibitive. These devices are relatively sophisticated and will require attention from skilled operators to ensure their proper functioning.

The objective of the present invention is to provide an air sampler for field use that is relatively simple and cost effective in large scale operations and which overcomes many of the disadvantages associated with using solid sorbent tubes.

SUMMARY OF THE INVENTION

According to the present invention there is provided an air, gas or vapour comprising:

a magizine adapted to house plural sampling tubes, said magizine having an inlet and an outlet at a sampling position thereof;

tube advancing means for sequentially advancing tubes in the magazine to and then from the sampling position;

tube sealing means at the sampling position selectively operable to seal the inlet to one end of a sampling tube at the sampling position and to seal the outlet to the other end of the sampling tube at the sampling position;

an air pump connected to the outlet for drawing through the inlet, the sampling tube at the sampling position, and the outlet;

control means for sequentially operating the tube advancing means to present a sampling tube to the sampling position, the tube sealing means to seal the inlet and outlet to the end of the sampling tube at the sampling position, the the pump to draw ambient air through the sampling tube at the sampling position, and the sealing means to disengage the inlet and outlet from the sampling tube.

The operation of the sampler is therefore completely automatic. The sampling tubes are protected from the environment, with the sole exception of the sampling tube at the sampling site. Through the use of plural tubes in an automatic arrangement, the changes in contaminants and their concentrations can be monitored. Where small-sized sampling tubes are employed as in the preferred embodiment, the volume of air sample required is reduced, so requiring a relatively low, early controlled flow rate which can be achieved with smaller less expensive pumps and components which require only a low battery power to operate. It is also possible to have an efficient thermal desorption using direct heating, without cold trapping, to produce quantitative chromatographic data. The equipment size and complexity is also reduced.

The use of a magizine to house the sampling tubes protects the outer surface of the sampling tubes from direct exposure to the sampled atmosphere, thus avoiding inadvertent contamination and passive sampling during storage.

Furtherfmore the magazine is used both as a sample transport and a storage container forming an integral link between air sampling devices and thermal desorption analytical equipment.

BREIF DESCRIPTION OF THE DRAWINGS

In the accompanying drawings, which illustrate an exemplary emobodiment of the present invention.

DETAILED DESCRIPTION

Figure 1:
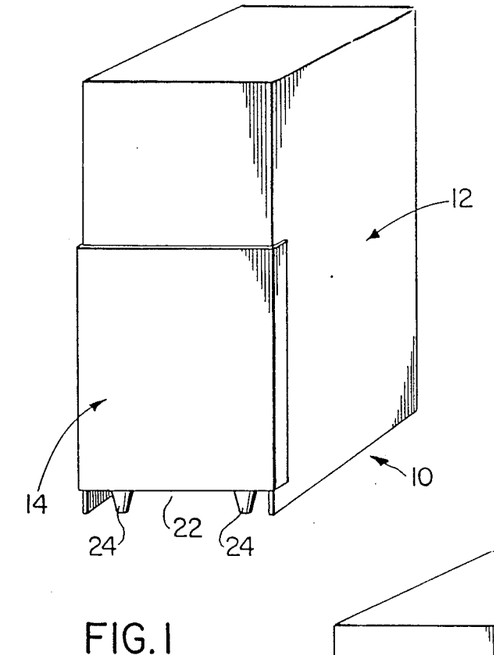
FIG. 1 is a perspective view of a sampler in a closed condition.
Figure 2:
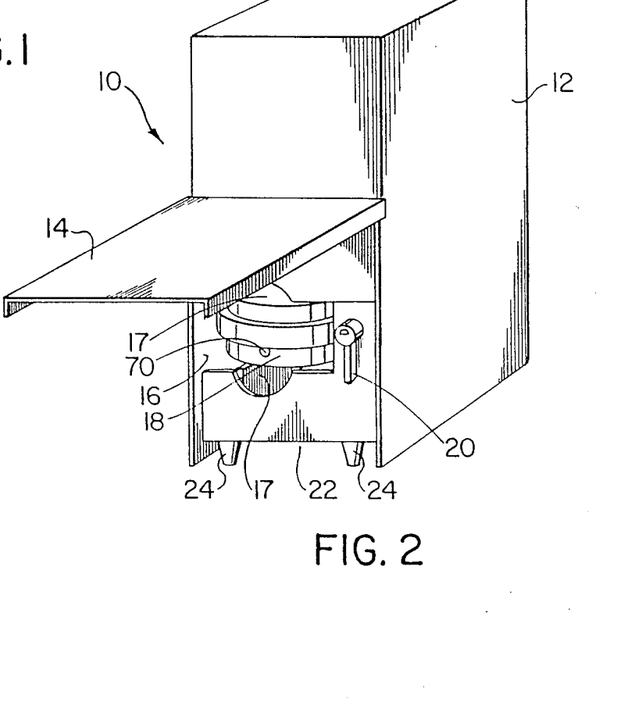
FIG. 2 is a perspective view of the sampler with its cover in an open condition and a magizine installed.
Figure 3:
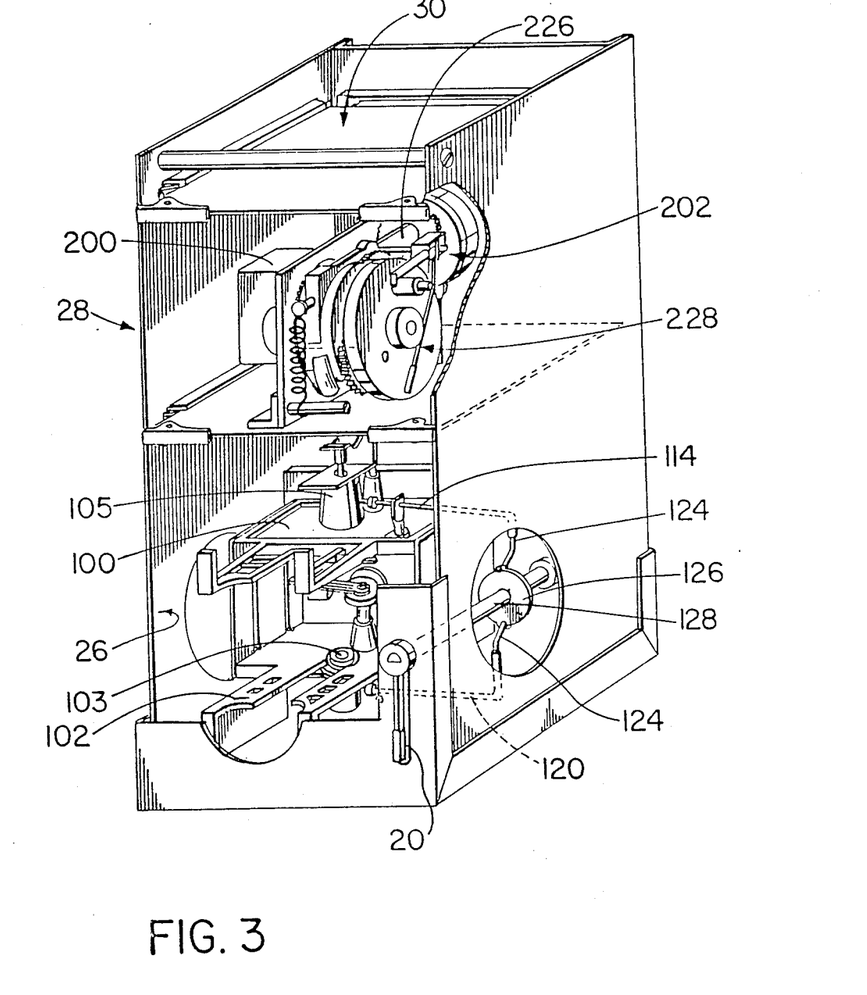
FIG. 3 is a perspective view of the sampler with its outer cover completely removed and partly broken away to show the arrangement of the internal components.

Referring to the drawings, and in particular to FIGS. 1, 2 and 3, there is illustrated a sampler 10 contained within an outer housing 12. The housing includes a front cover 14 pivotally connected to the front of the housing to swing up into the position illustrated in FIG. 2. A spring mechanism (not illustrated) associated with the hinge retains the cover 14 in either the position illustrated in FIG. 1 or that illustrated in FIG. 2. Under the cover 14, the front of the sampler has a magazine slot 16 that is rectangular overall, with two semi-circular finger notches 17 at the top and bottom. The slot 16 accommodates a short, cylindrical magazine 18. Beside the magazine slot 16 is a release lever 20 that is turned through 180° to release a magazine 18 from the sampler and to receive a new magazine.

The front face of the sampler has its bottom edge spaced above the bottom edge of the sides so that sampler there is a gap 22 left at the bottom, front of the sampler to admit air to be sampled. The sampler is supported on feet 24, two of which are illustrated in FIG. 1 and 2. The sample may also be suspended from a pole using a handle means (not shown).

As illustrated most particularly in FIG. 3, the sampler has three sections internally. The lower most of these is an indexer section 26 where magazines are retained in use. Above this is a pump section 28 containing a pump for drawing air through the sampling tubes. Above the pump section is a printed circuit board 30 that provides the control circuitry for the individual sampler.

Figure 9:
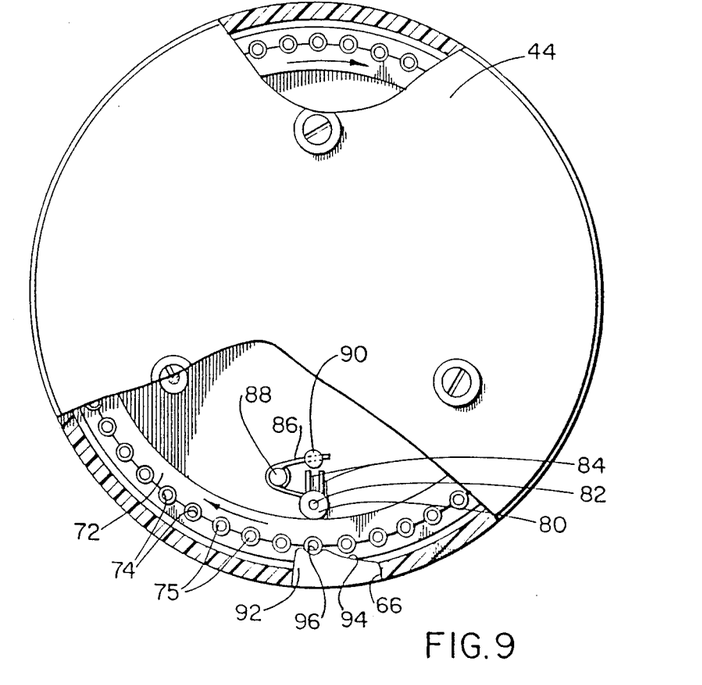
FIG. 9 is a plan view, partially broken away of a magazine.
Figure 10:
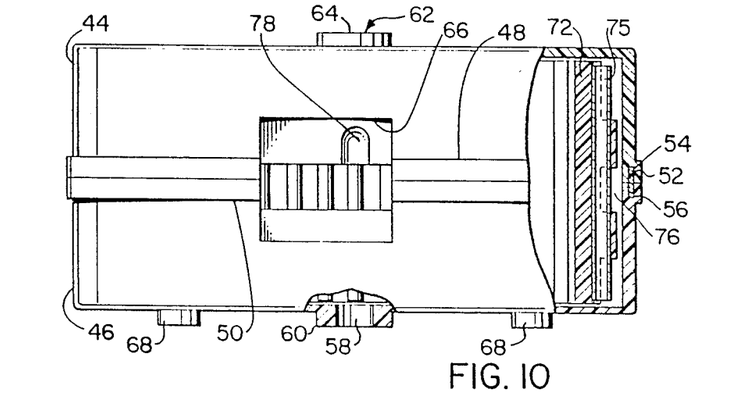
FIG. 10 is a front elevation, partially in section of the magazine.

Before discussing the indexer section in detail, it will be of use to examine the magazine, which is illustrated most particularly in FIGS. 9 and 10. The magazine consists of a plastic, cylindrical housing with a top section 44 that has a flat top and a cylindrical side wall and a simlar bottom section 46. The top section 44 and bottom section 46 have ribs 48 and 50 respectively, formed at their mating peripheral edges. The ribs are joined by a spline 52 seated in mating grooves 54 and 56 in the ribs 48 and 50 respectively.

The magazine 40 has an inlet port 58 in its bottom surface, adjacent the periphery. The port is surrounded by anannular boss 60. A coaxial outlet port 62 is formed on the top surface and is surrounded by a similar annular boss 64. In the side wall of the magazine, adjacent the inlet and outlet ports is a rectangular index opening 66. Two cylindrical locating bosses 68 protrude from the bottom of the magazine, and are arranged symetrically with respect to the inlet port 58. A small transparent window 70 is provided in the side wall of the magazine 40, directly opposite the index opening 66 (see FIG. 2).

Within the magazine there is a annular tube holder 72 with a large number of axially oriented tube holding bores 74 uniformly spaced around it. In the embodiment shown there are fifty tube holding bores. Each bore houses a respective sampling tube 75 which contains solid adsorbent as is well known in the prior art. The tube holder has a central peripheral groove 76 that exposes the centre section of each tube as it passes the index opening 66, as shown in FIG. 10. The tube holder is also provided with an indexing notch 78 in the face of the holder immediately above the peripheral groove 76. The tube holder is also numbered around its periphery, with the numbers being visible through the window 70. The numbers are arranged such that number 1 is displayed through the window when the index notch 78 is located centrally of the index opening 66.

Inside the magazine, within the tube holder 72, there is a biasing roller 80 with its axis parallel to the sampling tubes. The roller has an axle 82 at either end that is engageable between two parallel flanges 84 formed on the respective top or bottom of the magazine housing. To bias the roller towards the tube holder, a spring 86 is coiled around a stud 88 formed on the inside of the magazine, with one of its arms engaging a further stud 90 and the other arm riding on the axle 82 of the roller 80. The roller and its associated flanges and springs are located to press the tube holder against the inside of the magazine at the index opening 66. At the index opening, there are two seats 92, one above the index opening and one below it, which engage the individual tube at the index opening to ensure its proper alignment with the ports 58 and 62. Each seat has a camming face 94 that leads up to a concave notch 96 for its action on the tube holder 72 ensures that the tubes are properly seated in the two seats.

Reverting now to FIGS. 3 and 6 through 8, the indexer section 26 of the sampler includes an upper frame element 100 and a lower frame element 102 that cooperate to retain the magazine in its proper position. The lower frame element 102 has a groove 103 in its upper face to accommodate the annular boss 60 around the inlet port of the magazine. A similar groove 103 is formed in the under side of the upper frame 100. An upper magazine locator 104 is fitted slideably in a locator sleeve 105 projecting from the top of the upper frame element 100. The upper locator has a cylindrical body 108 and a coaxial locking sleeve 110 (FIG. 8) projecting from its bottom surface. An L-shaped bracket 112 is fitted to the top of the upper locator sleeve 105. A similar lower magazine locator 106 is fitted slideably in a lower locator sleeve 107 on the bottom surface of the lower frame element 102. The two sleeves and the two locators are coaxial.

The lower locator 106 has a cylindrical body 116 and a locking sleeve 118 that projects from the upper surface of the cylindrical body. As illustrated most particularly in FIGS. 3 and 6, the two locators are engaged with respective locking rods 114 and 120 that project into bores in the locators through aligned slots in the locator sleeves. These locking rods are engaged in respective fulcrum pins 115 and 121 secured to the upper and lower frame elements 100 and 102 respectively. The ends of the locking rod remote from the locators are connected to cranks 124 that in turn connect to a common rotor 126 mounted on a locking rod 128. The locking rod extends from front to back of the sampler housing and carries the locking handle 20 at its front end. As can be seen most readily from FIG. 6, rotating the locking rod 128 and the associated rotor 126 in the direction of the arrow will spread apart the outer ends of the locking rods 114 and 120, thus urging the upper and lower locators 104 and 106 towards one another. When a magazine is properly located between the upper and lower frame elements 100 and 102, this will project the locking sleeves 110 and 118 into the outlet and inlet ports of the magazine to secure the magazine in place.

Referring again to FIG. 8, the upper locator 104 carries an upper seal 130 that includes a tube 132 with an enlarged head 134 at it lower end and an elastomeric annular seal 136 on the bottom end of the enlarged head. A coil spring 138 surrounds the tube 132 and bears, at its lower end, against the bracket 112. The upper end of the spring 138, bears on the under side of a collar 140 secured to the tube 132. A spring lever 142 extends through a slot 144 in the bracket 112 and has the upper end of the tube 132 extending through an opening in one of its ends. The other end of the lever 142 is also apertured to receive an operating rod 146 that carries a collar 148 beneath the lever 142. The rod 146 extends through an elongated guide 150 projecting from the top surface of the upper frame element 100. As illustrated most particularly in FIG. 7, the bottom end of the rod 146 carries a cam follower 152 for engagement with a cam as will be described in more detail in the following.

On the upper surface of the lower frame element 102, adjacent the groove 103 is a boss 154. Mounted on the top of the boss 154, for rotation thereon is a rotor 156. An eccentric cam follower 158 is secured to the rotor and is normally located behind it as can be most readily seen from FIG. 8. The rotor also carries a blade-like pusher 160 that is rotatably mounted on the top of the rotor with a leading end protecting towards the front of the sampler and a back end that is connected by a coil spring 161 to an anchor towards the rear of the sampler.

Behind the rotor 156 and below the follower 152 is a cam member 162. This is mounted for rotation about a horizontal axis oriented front to back of the sampler. The cam member 162 has an eccentric cam 164 that engages the follower 152 to raise the follower and the operating rod 146. The cam member 162 also has bevelled face plate 166 that engages the lower edge of the rotor 156 to give the rotor a partial rotation in the counter-clockwise direction as seen from above. A microswitch 168 (FIG. 6) is also operated by the cam 164.

Mounted to the underside of the upper frame element 100 is a further microswitch 170. This switch has a switch operator that projects into the space above the pusher 160 for engagement with the index notch 78 of the magazine to signal the "home" position of the magazine.

An inlet tube 172 leads from the bottom of the sampler housing to the lower locator 106. The tube communicates with the centre of the locking sleeve 118. Where it is surrounded by an annular seal 174. The upper end of seal 130 is connected to a tube 176 that leads to the pump unit 28 of the sampler.

Figure 4:
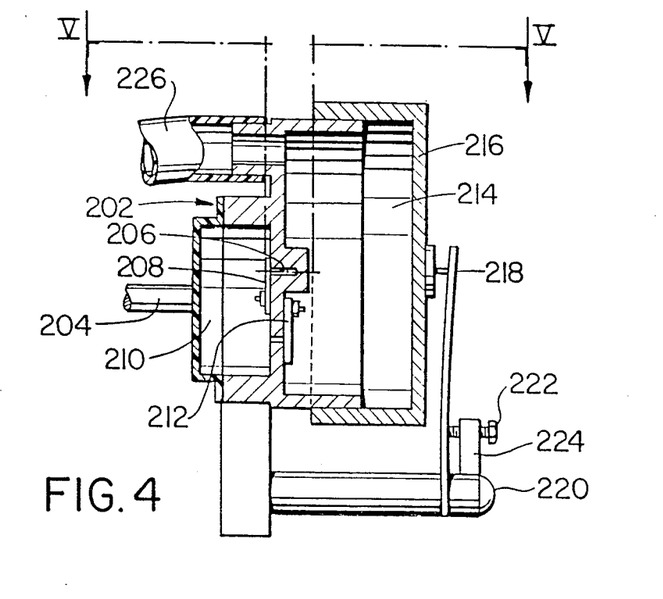
FIG. 4 is a side elevation, partially in section, of a boost pump.
Figure 5:
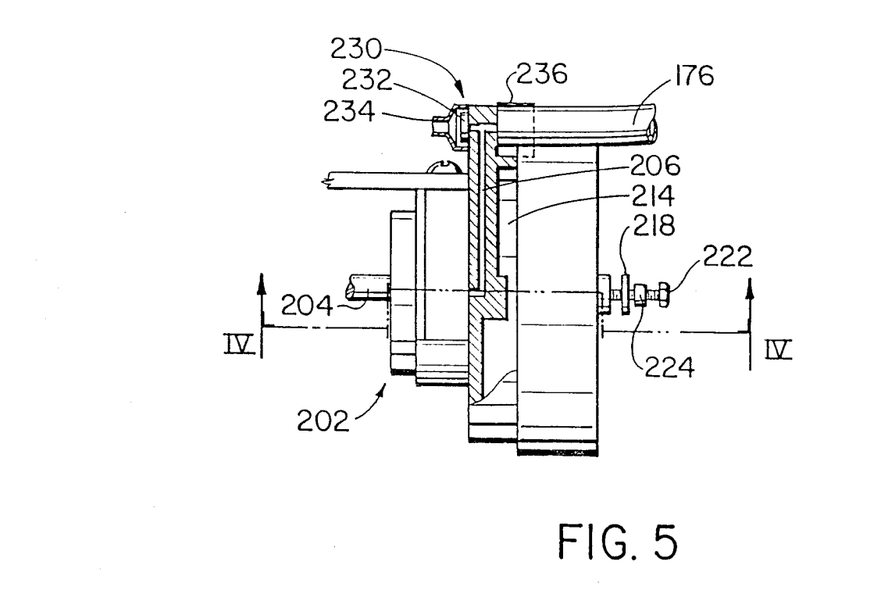
FIG. 5 is a plan view, partially in section, of the boost pump.

The pump section 28 of the sampler is illustrated most particularly in FIGS. 3, 4 and 5. The pump section includes a pump motor 200 that operates a diaphragm boost pump 202 through a connecting rod 204. On an intake stroke, air to the boost pump is drawn from tube 176 through an inlet passage 206 and check valve 208 into pump chamber 210. On a compression stroke, air is driven from the chamber 210 through a check valve 212 into a constant pressure chamber 214. One wall of chamber 214 is a diaphragm 216 that is subjected to constant pressure by one end of a leaf spring 218 bearing on a stud mounted on the centre of the diaphragm. The other end of the spring is fixed to the pump support by a stud 220, while a screw 222, threaded into a lug 224 and bearing on the spring, serves to adjust the spring pressure and thus, the pressure in chamber 214.

Air is supplied from chamber 214 to the inlet tube 226 of a peristaltic percision metering pump 228. Pumps of this sort are known per se. Metering pump 228 is driven directly by motor 200 and pumps air at a volumetric rate that is a direct function of the motor speed.

The inlet passage 206, leading to the boost pump is also connected to a blockage detector chamber 230 (FIG. 5). One wall of the chamber is a diaphragm 232 connected to an operating rod 234 for a switch 236. When a blockage occurs upstream, the pressure in passage 206 is reduced sufficiently by operation of the boost pump 202 that diaphragm 232 will be drawn in, to operate switch 236 and signal a blockage.

The electronic control part of the sampler 28 is a microprocessor based electronic control. This controls the operation of the various components of the sampler and may communicate with a host system controller to control the individual sampler according to an overall program for a multi-sampler system.

Figure 6:
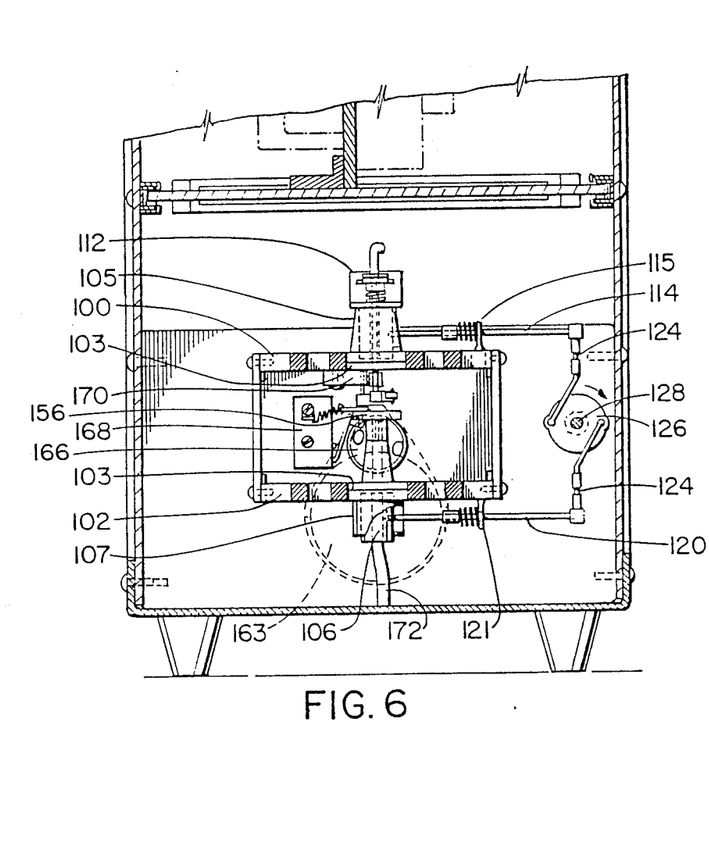
FIG. 6 is a front sectional elevation of the sampler.
Figure 7:
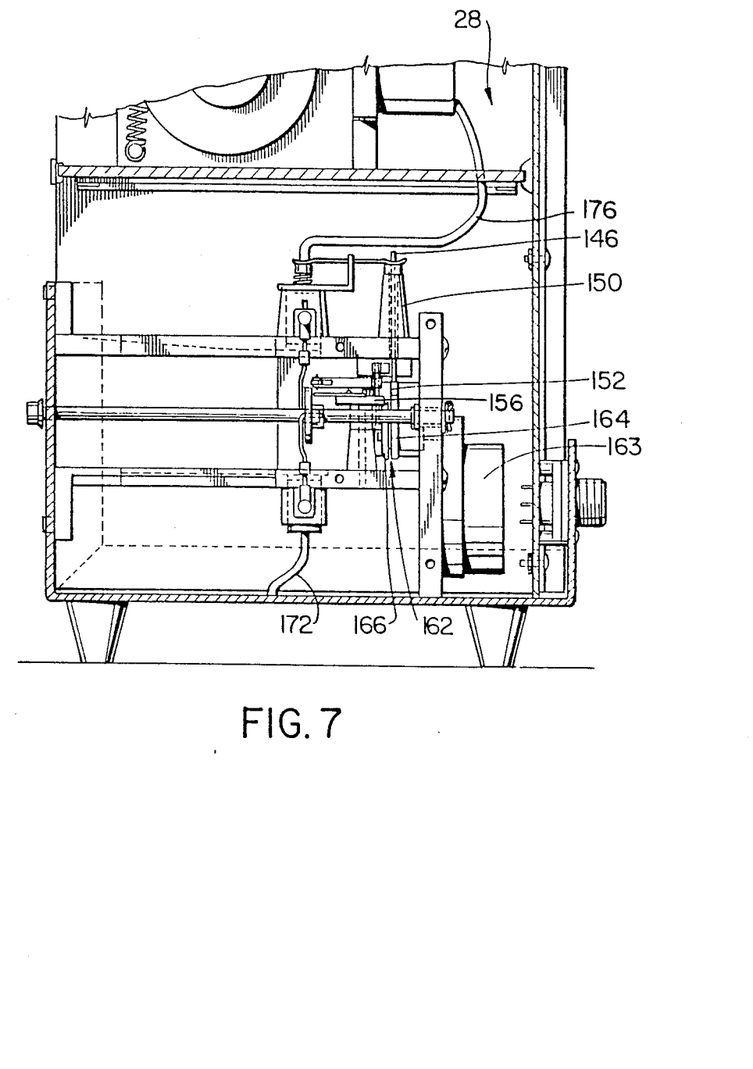
FIG. 7 is a side sectional elevation of the sampler.
Figure 8:
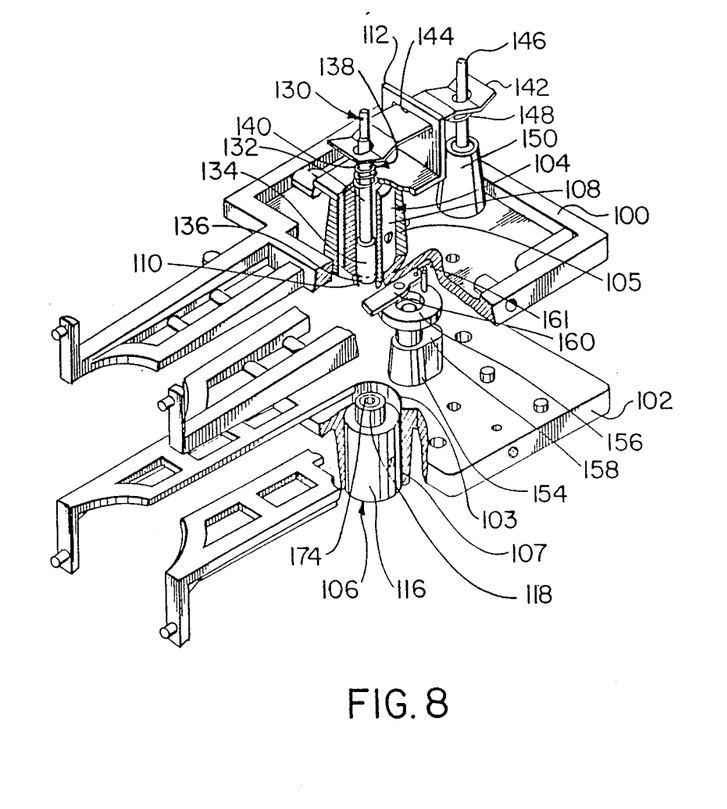
FIG. 8 is a detailed view, partially broken away of some of the indexer mechanism of the sampler.

To operate the sampler, the door 14 is opened and the handle 20 is pivoted counter-clockwise until the rotor 126 and the cranks 124 are positioned as shown in FIG. 6. This acts to retract the upper and lower locators 104 and 106 so that a magazine can be introduced between the upper and lower frame elements 100 and 102. The magazine is then inserted into sampler and seated with its inlet port 58 in alignment with the lower locking sleeve 118, its outlet port 62 in alignment with the upper locking sleeve 110, as shown at (a) in FIG. 12. In this condition, the two locating bosses 68 engage opposite sides of the lower frame element. The locking handle 20 is then rotated back to the position illustrated in FIG. 3. This advances the two locators 104 and 106 towards one another so that the upper and lower locking sleeves 110 and 118 engage in the outlet and inlet ports 62 and 58 respectively of the magazine, as shown at (b) in FIG. 12. The control system then operates the motor 163 (FIGS. 6 and 7) to rotate the multifunction cam 162 so as to drive the cam follower 152 and the associated rod 146 upwards, thus displacing the lever 142 and driving the upper seal 130 down against the top end of a sampling tube in the magazine, aligned with the outlet port 62. This displaces the tube downwardly against the seal 174 to seal the inlet tube 172 to the inlet of the sampling tube, as shown at (c) in FIG. 12. The pump is then operated, with the boost pump 202 drawing air to be sampled through the inlet tube 172, the sampling tube, the upper seal tube 132 and thence to the pump, as schematically illustrated at (d) in FIG. 12. The constant pressure diaphragm 216 associated with the boost pump controls the output pressure of the boost pump so that it is a desired constant, while the peristaltic pump meters the constant pressure flow to ensure that only a predetermined quantity of air is drawn through the sampling tube.

At the end of the sampling cycle, the pump is shut off, the cam 162 is rotated to release the sealing pressure on the ends of the sampling tube, as shown at (e) in FIG. 12, and to rotate the rotor 156 to index the magazine.

Figures 11A, 11B, 11C:
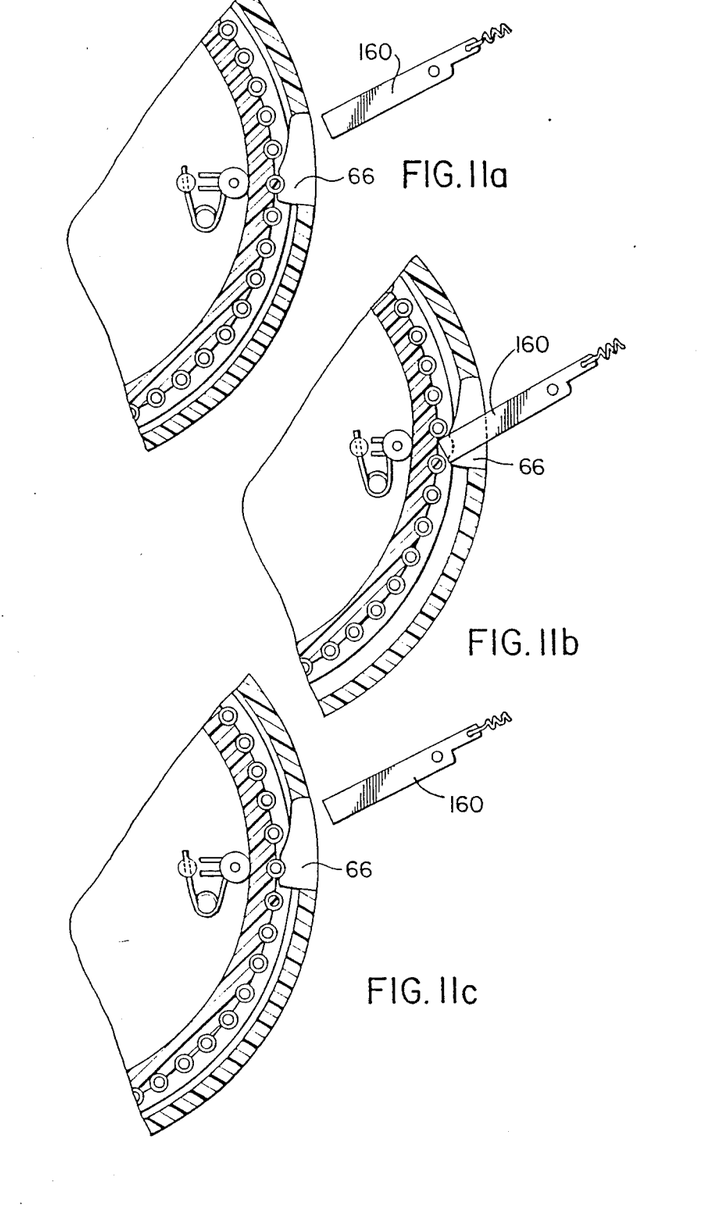
FIGS. 11a-11c are partial views of the magazine, showing the operation of the indexing means.
Figure 12A:
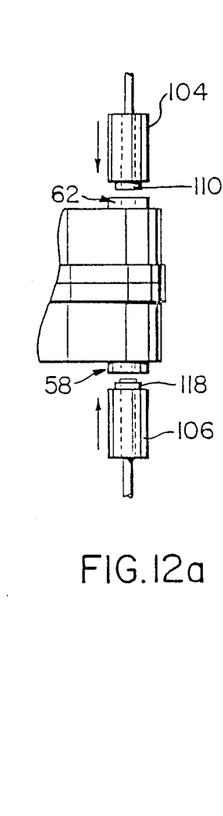
FIGS. 12a-12f para are schematic views showing the operation to the sealing means.
Figure 12B:
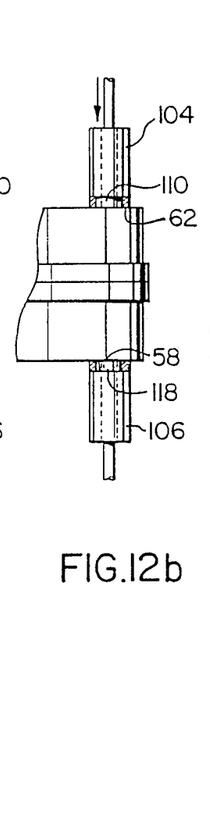
Figure 12C:
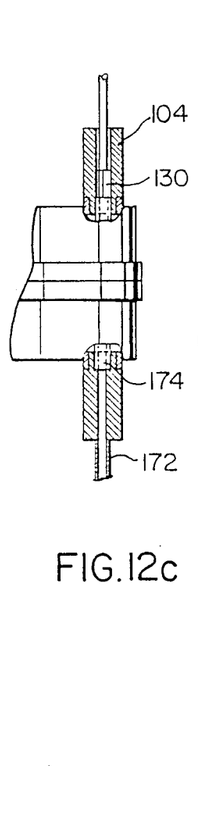
Figure 12D:
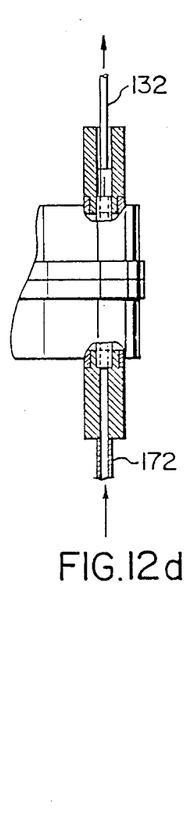
Figure 12E:
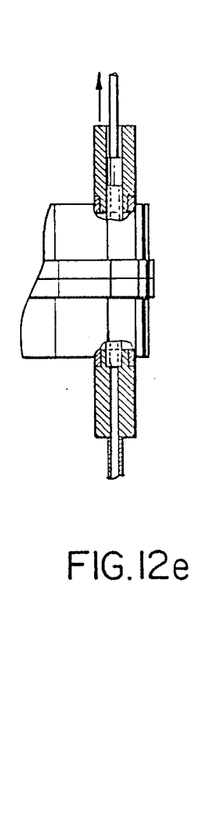
Figure 12F:
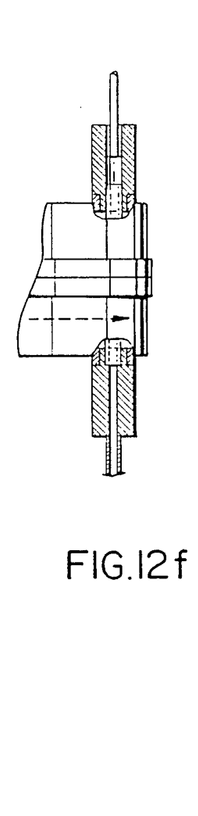

Indexing of the magazine is shown schematically in FIG. 11. At (a), the magazine and the pusher are in their initial positions, with a tube labelled "1" aligned with the magazine ports. Rotation of rotor 156 drives the pusher 160 into engagement with the sampling tubes through the index opening 66 in the magazine, as illustrated at (b) in FIG. 11. This rotates the tube holder by a distance equal to the spacing of adjacent tubes, to bring the next tube into the seats at the inlet and outlet ports, as shown at (c) in FIG. 11. The rotor is then allowed to return to its original position and the cycle is repeated.

In the event that there is a blockage in the air inlet it is detected by the blockage detector 230 which sends a signal, via switch 236, to the apparatus control circuitry. The sampler may then be shut down or indexed to another tube.

Once the magazine has cycled through all of the tubes, the index switch 170 detects the index notch 78 in the tube holder and provides an appropriate signal to the sampler controls to shut off further sampling. The index switch can also be used when a new magazine is installed in the sampler to provide a signal when the magazine is at its "start" position. This means that the tubes can be indexed to the "start" position at the beginning of a sample run.

The sampler may be connected to other samplers through a central control to provide a timed sampling of air over a wide area.

We claim:

1. An air sampler, comprising:
   a magazine having housing means for supporting plural sampling tubes, said magazine having an inlet and an outlet at a sampling position thereof, the housing means being rotatable about a rotational axis and supporting the tubes parallel to the rotational axis;
   tube advancing means for sequentially advancing the tubes in the magazine to and then from the sampling position by rotating the housing means about the rotational axis;
   tube sealing means at the sampling position selectively operable to seal the inlet to one end of a sampling tube at the sampling position and to seal the outlet to the other end of the sampling tube at the sampling position;
   an air pump connected to the outlet for drawing ambient air through the inlet, the sampling tube at the sampling position and the outlet; and
   control means for sequentially operating the tube advancing means to present a sampling tube to the sampling tube to the sampling position, the tube sealing means to seal the inlet and outlet to the ends of the sampling tube at the sampling position, the pump to draw ambient air through the sampling tube at the sampling position, and the sealing means to disengage the inlet and outlet from the sampling tube.

2. An air sampler according to claim 1 wherein the housing means of the magazine comprises an annular tube holder mounted for rotation in a magazine housing.

3. An air sampler according to claim 2 wherein the magazine has axially aligned inlet and outlet ports.

4. An air sampler according to claim 3 wherein the magazine has seating means adjacent the ports for retaining a tube in alignment with the ports.

5. An air sampler according to claim 4 including resilient means retaining a sampling tube in the seating means.

6. An air sampler according to claim 5 including an indexer opening in a peripheral wall of the magazine housing, between the ports, the tube holder has a peripheral groove aligned with the indexer opening, and the tubes extend across the groove and the indexer opening.

7. An air sampler according to claim 6 wherein the tube sealing means comprises two annular elastomeric seals engageable with opposite ends of a sampling tube at the sampling position and means for advancing one seal into and out of engagement with a respective end of a sampling tube at the sampling position.

8. An air sampler according to claim 6 wherein the tube advancing means include means for engaging a sampling tube at the sampling position through the indexer opening, displacing the engaged sampler tube out of the sampling position by rotating the tube holder so bringing another sampling tube to the sampling position.

9. An air sampler according to claim 1 wherein the air pump includes a boost pump for drawing air through sampling tubes and discharging the air at a predetermined pressure.

10. An air sampler according to claim 9 wherein the air pump includes a metering pump for drawing air from the boost pump at a predetermined flow rate.

11. An air sampler according to claim 10 including means for sensing a blockage in the air flow to the air pump.

* * * * *